[19] United States Patent
Schwarz

[11] Patent Number: 4,969,474
[45] Date of Patent: Nov. 13, 1990

[54] INCONTINENCE BLADDER CONTROL METHOD AND APPARATUS

[76] Inventor: Gerald R. Schwarz, 3710 SW. Scholls Ferry Rd., Portland, Oreg. 97221

[21] Appl. No.: 256,650

[22] Filed: Oct. 11, 1988

[51] Int. Cl.$^5$ ............................ A61F 5/48; A61F 2/02
[52] U.S. Cl. ...................................... 128/885; 600/30; 600/31
[58] Field of Search ...................... 128/885, 886, 868; 600/29, 30, 31; 623/11, 12, 23; 604/320, 321

[56] References Cited

U.S. PATENT DOCUMENTS

| | | | |
|---|---|---|---|
| 2,101,273 | 12/1937 | Smith | 128/DIG. 25 |
| 2,494,393 | 1/1950 | Lamson | 128/DIG. 25 |
| 2,638,093 | 5/1953 | Kulick | 600/29 |
| 3,538,917 | 10/1970 | Selker | 128/DIG. 25 |
| 3,646,929 | 3/1972 | Bonnar | 600/29 |
| 3,744,063 | 7/1973 | McWhorter et al. | |
| 3,815,576 | 6/1974 | Balaban | |
| 3,841,304 | 10/1974 | Jones | 128/DIG. 25 |
| 3,854,469 | 12/1974 | Giori | 128/DIG. 25 |
| 3,863,622 | 2/1975 | Buuck | 128/DIG. 25 |
| 3,881,199 | 5/1975 | Treace | 623/12 |
| 4,019,499 | 4/1977 | Fitzgerald | 600/30 |
| 4,044,401 | 8/1977 | Guiset | 623/12 |
| 4,056,095 | 11/1977 | Rey et al. | |
| 4,178,915 | 12/1979 | Szinicz | |
| 4,222,377 | 9/1980 | Burton | |
| 4,256,093 | 3/1981 | Helms et al. | |
| 4,360,007 | 11/1982 | Levy et al. | |
| 4,412,530 | 11/1983 | Burton | |
| 4,417,567 | 11/1983 | Trick | 600/31 |
| 4,419,985 | 12/1983 | Trick | 128/DIG. 25 |
| 4,449,520 | 5/1984 | Palomar | 623/12 |
| 4,552,128 | 11/1985 | Haber | 128/DIG. 25 |
| 4,571,749 | 2/1986 | Fischell | |
| 4,587,954 | 3/1986 | Haber | 128/DIG. 25 |
| 4,619,245 | 10/1986 | Haber | 128/DIG. 25 |
| 4,682,583 | 7/1987 | Burton | 600/31 |
| 4,773,393 | 9/1988 | Haber | 600/30 |
| 4,773,908 | 9/1988 | Becker | 600/31 |
| 4,822,333 | 4/1989 | Lavarenne | 623/12 |
| 4,828,544 | 5/1989 | Lane | 600/31 |
| 4,832,680 | 5/1989 | Haber | 600/31 |

FOREIGN PATENT DOCUMENTS

| | | |
|---|---|---|
| 7340939 | 11/1973 | France. |
| 89/00030 | 1/1989 | PCT Int'l Appl. ................. 600/29 |
| 1174814 | 2/1967 | United Kingdom. |

Primary Examiner—Robert A. Hafer
Assistant Examiner—Michael Brown
Attorney, Agent, or Firm—Marger, Johnson, McCollom & Stolowitz, Inc.

[57] ABSTRACT

A method and apparatus for controlling urinary incontinence in a patient includes positioning a reservoir containing fluid subcutaneously over the patient's anterior pubis; an inflatable compression balloon between the patient's posterior pubic symphysis and urethra; and a conduit extending over the pubis for fluid communication between a reservoir and a compression balloon. The compression balloon is inflated in response to fluid flow from the reservoir, when manually compressed by the patient. A manually releasable, one-way valve positioned in the conduit between the reservoir and a compression balloon retains fluid in the compression balloon under pressure and is externally actuable by the patient for equilibrating pressure in the reservoir and compression balloons to permit voiding. The bladder of the patient is elevated and connected anteriorly to the patient's abdominal wall by a felt matrix or mesh patch affixed to the bladder to effectively lengthen and stabilize the urethra. The compression balloon is arranged and positioned to compress in an inferior-posterior direction solely against an extended area the anterior side of urethra for occluding the urethra.

15 Claims, 3 Drawing Sheets

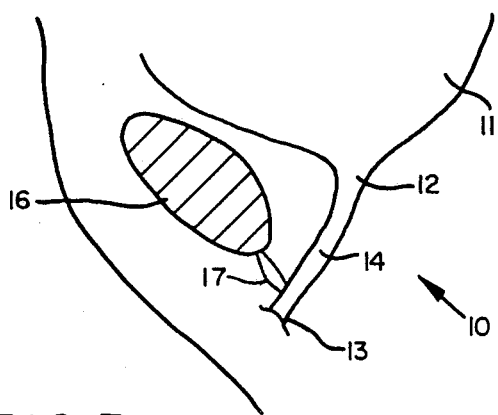
FIG. 1
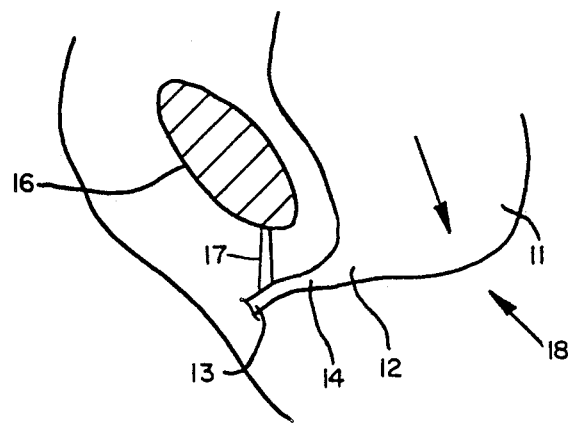
FIG. 2
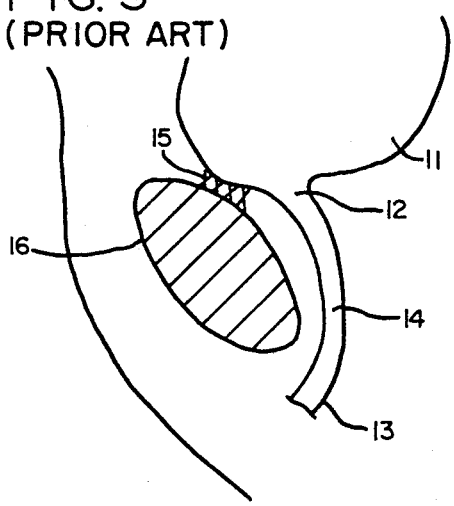
FIG. 3
(PRIOR ART)
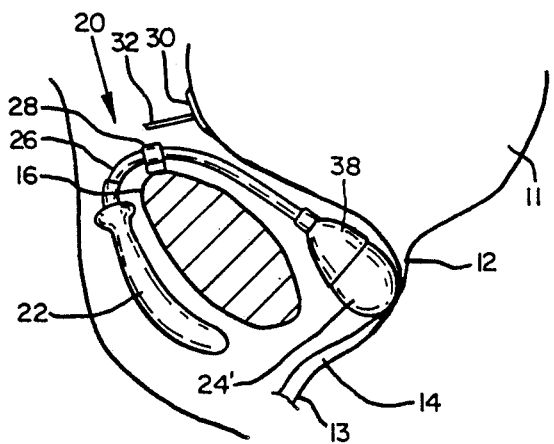
FIG. 4
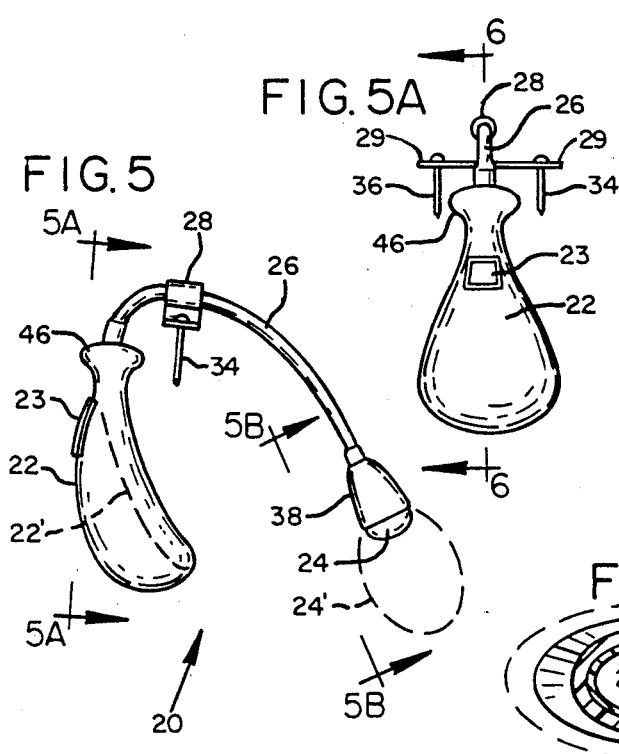
FIG. 5
FIG. 5A
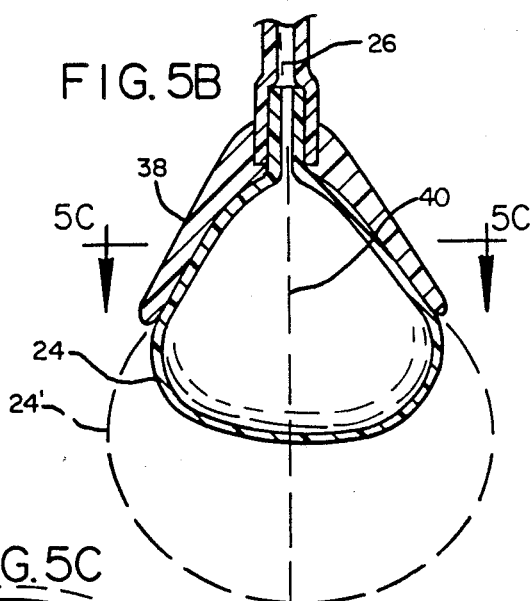
FIG. 5B
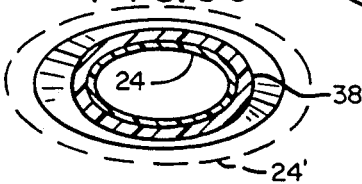
FIG. 5C

INCONTINENCE BLADDER CONTROL METHOD AND APPARATUS

BACKGROUND OF THE INVENTION

The present invention pertains generally to the treatment of urinary incontinence and more particularly to an incontinent bladder control method and apparatus incorporating a prosthesis for selectively restricting urine flow in a urethra.

Both males and females have an external sphincter formed about the urethra which, when functioning normally, constricts the urethra and prevents flow of urine from the bladder except when the bladder is voided during normal urination.

Urinary incontinence may result from several causes. For example, in females stretching or lengthening of the pelvic attachments t the bladder and urethra (termed cystocele or urethrocele) may occur, such as following a normal vaginal parturition, thereby allowing the bladder to descend from a normal position (FIG. 1) into a lower position (FIG. 2) thus functionally shortening the urethra. This form of incontinence may be surgically corrected by re-securing the bladder and urethra into a normal or near-normal position in the pelvis (FIG. 3), thereby regaining normal or additional urethral length. In this type of incontinence, the essential elements of the sphincter are intact.

A more difficult form of urinary incontinence relates to iatrogenic injury to the urethral sphincter. Such injury is common in the male following certain types of prostate surgery (e.g., for prostate malignancy and sometimes for benign prostatic hypertrophy) and produces incontinence as result of damage to or loss of the external urethral sphincter. This form of incontinence is treated by repair or augmentation of the sphincter, or by substitution of its function by implantation of a prosthetic sphincter. It is not treatable by repositioning surgery, as in the case of female urethrocele/cystocele, because that surgery requires an intact sphincter.

There are numerous prior art prosthetic sphincters for selectively closing and opening the urethra to prevent incontinence. These devices typically incorporate an inflatable cuff which surrounds the urethra or encloses it on two sides, and which is inflated to restrict urine flow in the urethra. Examples of such prosthetic sphincters are seen in U.S. Pat. No. 4,571,749 to Fischell, U.S. Pat. No. 4,222,377 to Burton and in other prior patents referenced in the accompanying information disclosure statement.

Implementing this approach can encounter surgical difficulties and using it involves problems of control, both with potentially serious complications. Surgery in the female requires a difficult dissection behind the bladder neck and urethra, risking perforation of the adjacent vaginal wall. In males, dissection in this area encounters the prostate and rectum, risking rectal injury/fistula.

After implantation, control and maintenance of pressure in the cuff has been found to be difficult. Inadequate pressure (inflation) applied by such prior art devices may fail to occlude the urethra and thus permit continued incontinence. When sufficient pressure is applied, incontinence can be initially prevented but then may recur as result of partial tissue loss or necrosis of the urethra due to excessive localized pressure applied to the urethra by the prosthetic sphincter.

Another drawback associated with the prior art prosthetic sphincters, which are activated by transfer of an incompressible fluid, relates to the complex control systems used for inflating and deflating the sphincter. Examples of such prior art systems are seen in U.S. Pat. No. 4,571,749 to Fischell and in U.S. Pat. No. 3,744,063, which includes a fluidic control system for inflating and deflating an artificial sphincter that includes four check valves. Other examples are disclosed in the accompanying information disclosure statement. Accordingly, a need remains for a better way to treat urinary incontinence, particularly in males and in cases of iatrogenic injury to the external sphincter.

SUMMARY OF INVENTION

It is an object of the present invention to provide a method and apparatus for treatment of incontinent bladder function which overcomes the above enumerated disadvantages which are inherent in prior art devices and methods.

A further object of the invention is to provide a prosthesis which is simply constructed and which may be easily used by a patient to selectively restrict or permit urine flow in the urethra.

Another object is to provide such a urinary incontinence treatment method and apparatus capable of restricting urine flow without compressing the urethra to the extent that tissue loss or necrosis occurs.

Yet another object of the invention as aforesaid is to enable treatment of incontinence in both males and females in the same way and with similar effectiveness.

The apparatus of the invention comprises a reservoir containing fluid and an inflatable compression means positionable between the bone of a human pelvis and the urinary bladder and in fluid communication with the reservoir. A releasable one-way valve means is included between the reservoir and compression means for controlling and maintaining inflation of the compression means. The compression means is designed to fit between the posterior symphysis of the patient's pubis and anterior side of the patient's urethra. So positioned, inflation of the compression means compresses the urethra along one side and over an extended area to occlude the urethral lumen. Means for directing inflation of the compression means can be provided to direct expansion of the compression means preferentially in an inferior-posterior direction, i.e., parallel to the posterior symphysis pubis, to impinge upon the anterior aspect of the urethra.

The method of the instant invention comprises the steps of (a) elevating the patient's bladder, (b) elongating the urethra and (c) compressing a lengthwise extent of the urethra. This is preferably done by surgically implanting the inflatable compression means at the neck of the elevated bladder between the pubis and ventral side of the urethra and releasably inflating the compression means. Inflation of the compression means can be directionally channelled for urging the same against the urethra substantially along its length.

Placement and operational effectiveness of the compression means are aided by elevating the bladder. This functionally lengthens the urethra and reduces lumen size so that it can be occluded more easily by inflating the compression means. Inflation of the compression means on only one side of the urethra and over an extended area of its length minimizes risk of necrosis of urethral tissue. Additionally, because compression of the urethra is on one side and against lower abdominal contents, control will be at least partially responsive to intraabdominal pressure variations, e.g., due to bladder filling, coughing, so as to help maintain continence.

Further objects, features and advantages obtained by the instant invention will become more fully apparent when the following detailed description of a preferred embodiment is read in view of the accompanying drawing.

BRIEF DESCRIPTION OF DRAWINGS

FIG. 1 is a simplified diagram showing a lateral sectional view of a normal bladder and pubis of a human female in standing position.

FIG. 2 is a view similar to FIG. 1 showing a cystocele and urethrocele condition.

FIG. 3 illustrates a conventional surgical correction of the condition shown in FIG. 2.

FIG. 4 is a view similar to FIG. 1 showing a simplified diagram illustrating implementation of the present invention to correct urinary incontinence in either male or female.

FIG. 5 is a more detailed lateral view of the device shown implanted in FIG. 4.

FIG. 5A is a frontal elevation view taken along line 5A—5A in FIG. 5.

FIG. 5B is a longitudinal section view taken along line 5B—5B in FIG. 5.

FIG. 5C is a cross-sectional view taken along line 5C—5C in FIG. 5B.

DETAILED DESCRIPTION

Figure 10:
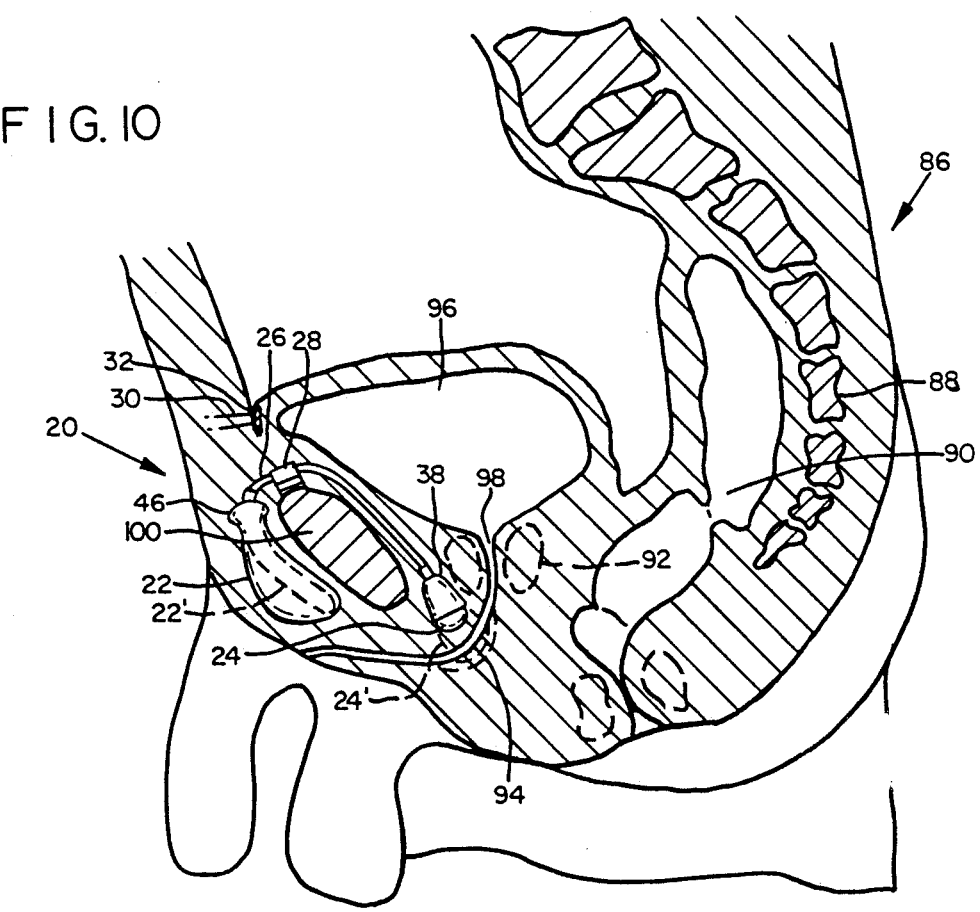
FIG. 10 is a male anatomic diagram similar to the view of FIG. 8, showing the compression balloon deflated in solid lines and inflated in dashed lines.

Turning now to the drawings, and more particularly to FIG. 1, indicated generally at 10 is a simplified diagram of a portion of normal anatomy of a female in standing position. Included in this lateral view is a bladder 11, bladder neck 12 and a urethra 14. Also included is the pubis bone 16. The distal end 13 of the urethra is a relatively fixed position by virtue of attachments 17 to the inferior pubic arch and anterior-superior vaginal tissues. A sphincter surrounding the urethra normally maintains the lumen or central opening through urethra 14 in a closed condition thereby preventing urine from traversing the urethra. Relaxing the sphincter opens the lumen to permit voiding of urine from bladder 11.

Turning now to FIG. 2, indicated generally at 18 is a view similar to FIG. 1 illustrating an anatomic defect which may occur in females and which is referred to as cystocele and/or urethrocele, producing "stress" incontinence. Structures corresponding to those previously illustrated and described in FIG. 1 bear the same numbers in FIG. 2.

The cystocele/urethrocele condition is defined as a downward migration of bladder 11, bladder neck 12 and urethra 14 from the normal position shown in FIG. 1 to the position shown in FIG. 2. Such migration is typically a result of a structurally inadequate muscular floor of the anterior pelvis. It is thought to be a normal aging process accelerated by pregnancy and vaginal delivery of the fetus. Stretching or lengthening of the pelvic attachments to the bladder and urethra permits bladder 11 and urethra 14 to descend into the lower position shown in FIG. 2.

When in the lowered position of FIG. 2 with its distal end 13 attached as indicated at 17, urethra 14 is effectively shortened and thus the lumen assumes a larger effective diameter. With the lumen diameter so enlarged, the sphincter itself may be distended, lack sufficient range and/or strength to fully occlude the lumen, thereby resulting in urinary stress incontinence.

Urinary incontinence of the cystocele/urethrocele type illustrated in FIG. 2 can typically be successfully corrected by various conventional surgical procedures. FIG. 3 illustrates the anatomy after successful surgical correction of the cystocele/urethrocele condition of FIG. 2. The procedure consists of elevating the bladder and fixing it by sutures 15 to the posterior surface of the superior pubic arch. This functionally lengthens the posterior surface of the urethra 14 by bringing bladder neck 12 and urethra back into a more superior and anterior position from the location shown in FIG. 2 while the attachments 17 retain the distal end 13 in place below pubis 16.

A more difficult form of urinary incontinence relates to iatrogenic injury which is common in the male following surgery for prostate malignancy, and, in some instances, surgery for benign prostatic hypertrophy. This form of incontinence is secondary to damage to or loss of the muscle and/or nerve elements of the external sphincter mechanism. Prosthetic surgery has been necessary to correct this type of defect since normal muscle and/or nerve supply is irreparably lost; thus, a substitute sphincter must be utilized. As discussed above, the prior art methods using artificial sphincters have various drawbacks that my invention avoids as next described.

Turning now to FIG. 4, indicated generally at 20 is a prosthetic device constructed in accordance with the invention implanted in a female. Anatomy corresponding to that previously identified in FIGS. 1-3 is identified with the same numbers in FIG. 4.

Generally speaking, device 20 includes a compressible reservoir balloon 22, an inflatable balloon 24, which functions as an inflatable compression means, and a tube 26 providing fluid communication between balloons 22, 24. A lateral attachment tab 28 fixed to the superior pubis 16 secures tube 26 and thus balloons 22, 24 in position as shown. A quantity of a suitable liquid is contained within tube 26 and balloons 22, 24. As more fully explained, a transfer of liquid into balloon 24 is used to selectively compress urethra 14 in an anterior-posterior direction in an area just above the location of the natural sphincter. The compression platform against which the urethra is compressed is ultimately the sacrum and coccyx with intervening rectum and pelvic viscera providing a buffer (see FIGS. 8-10). The total volume of fluid in the device 20 is controlled by adding fluid to or subtracting fluid from the device by inserting a noncoring needle through a self-sealing diaphragm 23 in the anterior wall of reservoir 22.

An important part of the surgical procedure of implanting device 20 includes fixing the anterior-superior bladder to the posterior rectus fascia above the level of the superior pubic rami. This is accomplished by sewing a 1 cm. by 2-3 cm. felt matrix or mesh patch 30 to the anterior bladder wall. The patch in turn is then sewn to the posterior aspect of the rectus fascia (not shown) via suture 32. Additional detail concerning the implantation of device 20 and the anchoring of the bladder via suture 32 is provided hereinafter. Attention is now directed to FIGS. 5, 5A, 5B, 5C, 6 and 7 for more detailed consideration of the structure of device 20.

Device 20, except for attachment tab 28 and a pair of staples 34, 36 which are used to anchor the lateral attachment tabs 29 of attachment 28 as shown in FIG. 4, is constructed of or encased by conventional plastic implantable material.

Reservoir balloon 22 is shaped to contain a relatively large volume of fluid while maintaining a relatively small anterior-posterior width as viewed in FIG. 4. The relatively wide lateral dimension of balloon 22, as viewed in FIG. 5A, overlies the broad expanse of anterior pubic bone 16 when implanted.

Compression balloon 24 similarly has a somewhat flattened shape with an oval cross section best seen in FIGS. 5B and 5C. This shape helps locate and maintain the compression balloon in position between the concavity of the pubic symphysis and the anterior urethra.

Figure 6:
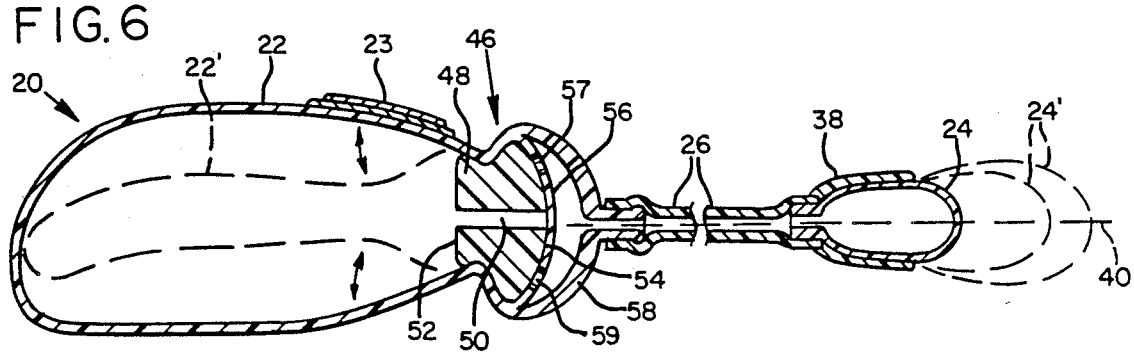
FIG. 6 is a sectional view taken along lines 6—6 in FIG. 5A showing interior details and operation of the first embodiment with the reservoir being inflated and compression balloon deflated in solid-lines and the reservoir deflated and compression balloon inflated in dashed lines.

In the first embodiment shown in FIG. 6, balloon 24 includes a restraining means or skirt-like cup 38 fixedly attached to tubing 26 as shown in FIG. 5B. As fluid moves from balloon 22 to balloon 24 via tube 26, in a manner which is hereinafter more fully described, cup 38 restricts expansion of balloon 24 to a direction substantially downwardly along an axis 40 in FIG. 5B. The dashed line outline 24' in FIG. 5B illustrates the configuration of the lower portion of balloon 24 when the same is further inflated from the solid-line view of FIG. 5B. The dashed line configuration is obtained because of the restraining action of cup 38 on the expansion of upper portion of balloon 24.

Figure 7:
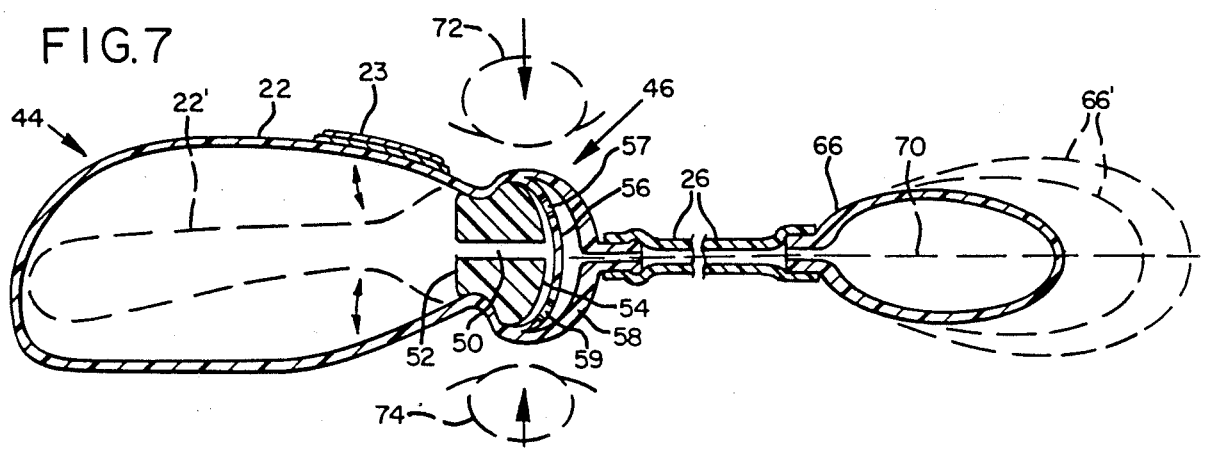
FIG. 7 is a view similar to FIG. 6 of a second embodiment of the invention, showing operation of the releasable check valve to equilibrate the reservoir and compression balloon to permit voiding.

FIGS. 6 and 7 are more detailed sectional views of device 20 and an alternate embodiment 44 respectively, constructed in accordance with the invention. Both embodiments of the invention as disclosed in FIG. 6 and FIG. 7 incorporate the same structure in balloon 22 up to and including the attachment of the same to tube 26. Thus, in the views of FIGS. 6 and 7 all structure to the left of the break-line in tube 26 is substantially identical in each embodiment and thus contain the same reference numerals in the various figures.

Referring to FIG. 6, a check valve 46 is incorporated into balloon 22 at the entrance to tube 26. In the example shown valve 46 includes a resilient cylindrical valve body 48 having an axial bore 50. One end of bore 50 communicates with balloon 22 along a substantially planar side 52 of valve body 48 while the other end of bore 50 communicates with tube 26 along an opposite convex or dome-shaped side 54 of the valve body. A resilient circular membrane 56 is attached about the circumference of side 54 to the inside of the wall of balloon 22 and, in the view of FIG. 6, is flushly sealed against side 54. Membrane 56 has pair of openings 57, 59 spaced radially apart from the center of the membrane and from axial bore 50. In the closed position shown in FIG. 6, a greater pressure on the right side of membrane 56 seals the membrane against dome 54 to block openings 57, 59 and prevent fluid flow from tube 26 to bore 50.

The embodiment of FIG. 7 illustrates check valve 46 in its open condition. Compression of valve body 48 via a patient's thumb 72 and forefinger 74 deforms the valve body 48 and lifts membrane 56. This action opens holes 57, 59, allowing fluid to flow via bore 50 into reservoir 22. Additional details concerning the opening of check valve 46 are provided hereinafter in connection with the description of operation of the various embodiments of the invention.

At its juncture with tube 26, balloon 22 forms a resilient connecting member 58. Member 58, as seen in FIGS. 6 and 7, includes thickened walls which resiliently maintains member 58 in a domed shape spaced axially from the valve body as shown in the drawing. The structure of valve 46 is believed to be known and, by itself, is not my invention.

When balloon 22 is compressed, as indicated by dashed lines 22', fluid is discharged through bore 50 and openings 57, 59 and tube 26 into the compression balloon, distending the compression balloon as indicated by dashed lines 24', 66'. When valve 46 is squeezed between the patient's fingers, sufficient fluid in the distended compression balloon flows back to the reservoir balloon to equilibrate the pressures in both balloons. The compression balloon thus contracts.

In the embodiment of FIG. 6, the inflatable balloon 24 has an entrance connected to tube 26 and has a wall of uniform thickness. Cup 38 is also shown fixedly connected to tube 26 with an upper portion including the entrance to balloon 24 retained inside cup 38. Cup 38 is made of an implantable material which is stiffer or thicker than the wall of balloon 24 and, as later described in more detail, does not deform when balloon 24 is inflated. Cup 38 functions to direct balloon expansion upon inflation so that greatest expansion occurs along the central axis 64 of tube 26, as indicated by dashed lines 24'.

In the embodiment of FIG. 7, an inflatable balloon 66 is fixedly attached to tube 26. The embodiment of FIG. 7 does not include a discrete retaining member, like cup 38 in FIG. 5B and FIG. 6, but functions in essentially the same manner. Unlike the wall of balloon 24 in FIG. 5B, the wall of balloon 66 varies axially in thickness. As can be seen, the thickest portion of the balloon occurs adjacent its attachment to tube 26. The wall tapers uniformly about the circumference of the balloon, down to minimum thickness at a latitude midway between the end of the balloon attached to tube 26 and the outermost balloon end. Thereafter, balloon 66 is formed of a substantially uniform thickness wall. With balloon 66 so formed, the outermost end of the balloon tends to expand more rapidly in response to balloon inflation than the remainder of the balloon. This causes maximum expansion of balloon 66 along the axis 70 of tube 26, as indicated by a dashed line 66' in FIG. 7.

Figure 8:
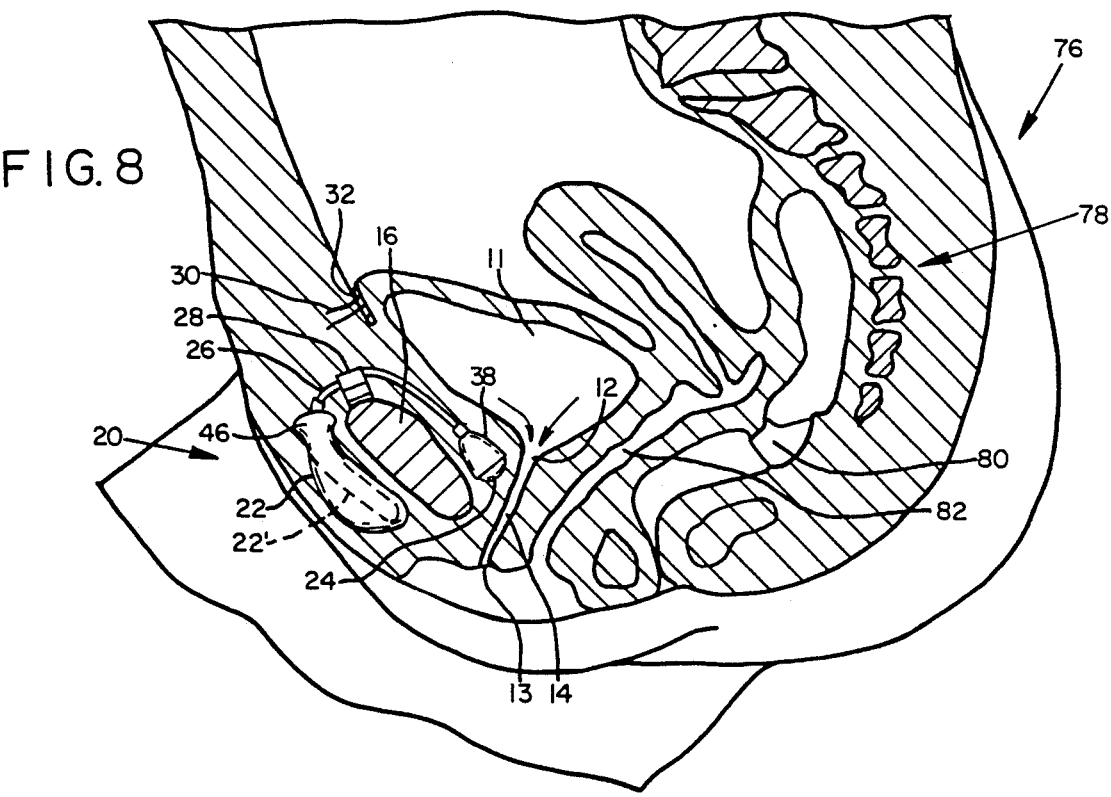
FIG. 8 is a more detailed female anatomic diagram similar to the view of FIG. 4 showing a device constructed in accordance with the invention in deflated condition to permit voiding.

Turning now to FIG. 8, device 20 is shown after being implanted in a female patient indicated generally at 76. Structure previously identified herein is identified with the same number in FIG. 8. Additional anatomical structure includes the coccyx 78, such comprising the lowermost portion of the spine. Also illustrated are the rectum 80 and vagina 82. In the view of FIG. 8, balloon 24 is shown in a substantially deflated or contracted condition.

Figure 9:
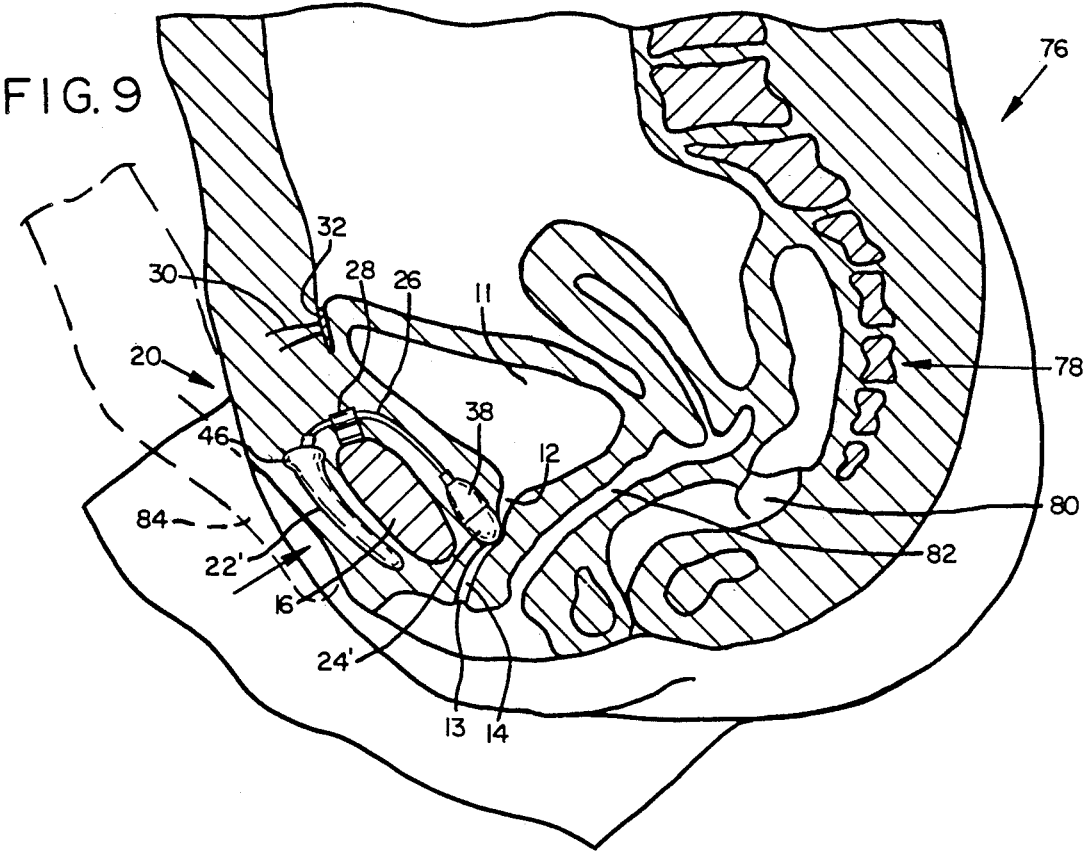
FIG. 9 is a view like FIG. 8 showing the compression balloon in a filled condition for occluding the urethra.

In FIG. 9, balloon 24 is illustrated in an inflated condition such that urethra 14 is compressed in an anterior-posterior direction between balloon 24 and the tissue posterior to urethra 14, thereby occluding the urethral lumen as illustrated. A portion of the patient's forefinger 84 is shown in dashed lines compressing the reservoir balloon 22 against the pubis 16. This action forces fluid from reservoir balloon 22 through tube 26 to inflatable balloon 24. The balloon 24 expands axially, preferentially compressing a lengthwise portion of the urethra.

In FIG. 10, device 20 is illustrated implanted in a male patient indicated generally at 86. Included in male patient 86 is a coccyx 88, a rectum 90 and a prostate gland 92, shown in dashed lines, encircling urethra 94. The urethra depends from bladder 96, there being a bladder neck 98 formed between the bladder and urethra 94. Device 20 is mounted via attachment tab 28 to pubis bone 100.

Surgical access for the implantation of the proposed incontinence device is via a standard lower vertical mid-line abdominal or horizontal (Pfannenstiel's) incision, with separation of the rectus muscles to gain access to the retropubic (anterior pelvic) space and to the superior pubic rami. Each of devices 20, 44 are attached to the anterior-superior aspect of the anterior pubic rami on either side of the symphysis pubis by staples 34, 36 driven into pubis 16 (pubis 100 in FIG. 10) through lateral attachment tabs 29. Reservoir balloon 22 is implanted in a subcutaneous pocket overlying the anterior pubic rami and symphysis in an area accessible to the patient for manual actuation (compression of the reservoir balloon). The underlying bone serves as a platform against which the reservoir is compressed.

Inflatable balloon 24 (or 66 in FIG. 7) is connected to reservoir balloon 22 over the superior aspect of the symphysis pubis via tubing 26. Attachment tab 28 is integrated with tube 26 and serves as the only point of fixation of the device to bone or adjacent structures. Balloon 24 is implanted behind the pubic symphysis and above the pubic arch within the retropubic space of the pelvis. Balloon 24 is positioned so that the bladder neck and urethra are compressed by it before the urethra passes through the pelvic diaphragm (not shown) under the pubic arch.

After separation of the rectus muscles via the earlier described standard surgical approaches, only blunt dissection may be necessary to gain access within the retropubic space for implanting the balloon 24 in a fixed relationship with the adjacent superior urethra and bladder neck. No dissection posteriorly or laterally of the urethra and bladder neck is necessary. This greatly simplifies the surgical procedure and avoids the possibility of rectal or vaginal injury. Venous structures in this area, particularly in the mid-line retropubic space, are numerous and large. Little or no dissection of these veins is required. Ligation, if necessary, or compression of these veins by the device 20, should not produce venous stasis since ample collateral veins are present laterally.

Balloons 24, 66 are narrow in the anterior-posterior dimension and wider in the lateral dimension, and oval in cross section to conform to the concavity of the posterior pubic symphysis. This shape stabilizes the compression device between the anterior bladder, bladder neck, and superior urethra posteriorly, and the concave posterior aspect of the pubic symphysis, anteriorly. The bladder as well as the pelvic contents hold the inflatable balloon in position behind the pubic symphysis at or near the mid-line. No additional fixation of device 20 to the posterior pubic bone or pelvic structure is necessary, as the shape of the device allows for stable positioning in this location within the concavity of the pelvis (between the diverging arms of the inferior pubic rami, anteriorly).

An integral and important part of the surgical procedure includes a means to affix the anterior-superior bladder to the posterior rectus fascia above the level of the superior pubic rami. Tube 26 is routed through the mid-line fascia through the incision between the rectus muscle bodies at or near their insertion on the superior aspect of the anterior pubic rami. The fascial incision is closed in standard fashion with interrupted sutures. The most inferior sutures bracket the interconnecting tubing as it exits the pelvis, thus securing fascial tissue around it and preventing herniation. Before fascial closure, a felt matrix or mesh patch 30 (in FIG. 4) of a biologically inert material, such as Dacron ®, is sewn to the anterior bladder wall over a distance of 2–3 cms. transversely. This, in turn, is sewn via suture 32, to the posterior aspect of the rectus fascia prior to the fascial closure, well above the rectus insertions and device 20. Tissue incorporation into the felt occurs both from the bladder aspect and the fascial aspect, effecting a secure union. This fixes the bladder to anterior structures (abdominal wall) thus stabilizing the bladder and urethra and preventing inferior migration of the bladder with expansion of balloon 24 as might otherwise occur. This concept is an extension of existing surgical principles with regard to stress urinary incontinence correction in the female.

In conjunction with this portion of the surgery, electrodes can be incorporated within the bladder wall, or affixed to it, to record the status of bladder filling via a strain gauge or similar instrument. This sensor, in turn, is linked to a warning device, for the patient who has deficient sensory enervation, or to nursing staff for the incompetent or incapacitated patient, to signal the need for voiding. The potential benefit of such a bladder warning system is great for institutionalized patients who are incapable of normal control (patients with Alzheimer's Disease, etc.). This requires a attentive nursing staff but would be a vast improvement over the incontinence that is often encountered in nursing home and convalescent center environments.

Because of the bladder fixation to be employed in this surgery, and the attendant temporary bladder dysfunction that is frequently seen with similar surgical procedures (e.g., for correction of stress incontinence in the female), it is likely that a temporary form of urinary drainage will be necessary in conjunction with the above described surgery and placement of a device constructed in accordance with the invention. A bladder catheter is placed in the mid-line through the fascial closure at a level higher than the placement of device 20 (again incorporated between fascial interrupted sutures). A Foley catheter or similar retention device is utilized for this purpose and is positioned adjacent the fixation felt 30 to aid in bringing the bladder into close opposition to the anterior abdominal wall via traction on the catheter during the post-operative period. This catheter is removed when voiding function is re-established and the patient is accomplished in the operation in the device and its voiding valve. At that time, the wound should be well-healed and the bladder well-fixed and stabilized anteriorly.

Reservoir balloon volume is carefully monitored at the time of surgery to ensure that adequate bladder emptying is possible when inflatable balloon 24 (in devise 20) is deflated, or at equal pressure with the reservoir. A portion of the reservoir balloon that is accessible from the anterior-superior aspect of this prosthesis component is designed with a self-sealing diaphragm 23 to allow perforation by a non-coring needle introduced through adjacent skin to add or subtract fluid volume.

With reference to FIGS. 8 and 9, after the device is implanted and the patient wishes to close the urethra to prevent bladder voiding, forefinger or fingers 84 is used to compress balloon 22 against pubis 16. When such compression occurs, as shown in FIGS. 6 and 7, fluid in balloon 22 is forced through bore 50. The increased pressure distends membrane 56 away from side 54 of valve body 48 thereby allowing fluid flow from bore 50 through holes 57, 59, and into tube 26 thereby inflating compression balloon 24, 66 and ultimately compressing the urethra between the balloon and the tissue posterior to the urethra. When the patient removes his or her finger(s), back pressure of the fluid in the compression balloon seals membrane 56 against the bore 50, blocking back flow of fluid.

When the patient desires to void his or her bladder, the patient can compress valve body 48 between his or her thumb 72 and forefinger 74 as shown in FIG. 7. Such compression lifts membrane 56 away from side 54 of the valve body thereby permitting flow from compression balloon 24 through tube 26 and holes 57, 59 in membrane 56. The fluid passes through bore 50 and back into reservoir balloon 22, thus allowing the device to resume the configuration shown in FIG. 8. With the balloon no longer inflated, the urethra opens, permitting voiding. After voiding, the patient again compresses the reservoir balloon with his or her forefinger to inflate balloon 24 thereby occluding the urethra lumen, as illustrated in FIG. 9, to prevent incontinence.

Since the inflatable balloon in each embodiment expands primarily along the longitudinal axis of tube 26, increasing expansion is directed in an inferior direction perpendicular to the pelvic diaphragm (not shown). Compression of the superior urethra results from expansion of the inflatable balloon over a broad surface area. The risk of tissue necrosis is minimal since the urethra is compressed only in the inferior-posterior direction and only with sufficient fluid transfer to effect continence. The compression is directed only upon the anterior wall of the urethra, ultimately compressing the urethra against the sacrum and coccyx posteriorly, with intervening rectum and pelvic contents providing a buffer.

With balloon 24 inflated, the urethra, already elongated and stabilized, is compressed and further lengthened as it is urged posteriorly by the expanding balloon. As the urethra is lengthened, the diameter of the lumen therein decreases, thus requiring less force to occlude the same. The area of compression of the urethra exceeds the anatomic size of the external sphincter in males. The locus of compression is immediately above the urogenital diaphragm (above the external sphincter) in the male. Since the inflatable balloon 24 is secured only by attachment tab 28, it is somewhat mobile. This mobility permits the balloon to be forced into a more inferior position with sudden increased abdominal pressure (such as with coughing, sneezing, etc.) or as directed by the patient (via voluntary Val Salva maneuver) to effect increased urethral compression. This voluntary patient maneuver can be utilized in the competent patient having intact bladder sensation in circumstances such as sudden bladder contraction.

It can be seen that the invention provides a bladder incontinent control method and apparatus which is easily operated and controlled by the patient. The patient controls both the degree of urethral compression, via incremental transfer of fluid from the patient-accessible reservoir balloon, and voiding function. The latter is effected by the patient or nursing personnel by a single manipulation which effects rapid urethral decompression. Another advantage of this invention is the ease of surgical access via standard anterior lower abdominal approaches, avoiding lateral and posterior dissection around the urethra and bladder neck. The concept utilizes urethral compression over a broad area at the highest level feasible, i.e., at the bladder neck and superior urethra. This allows the use of the proposed device in patients who have failed inflatable cuff applications or other surgical treatments at a lower level.

Having illustrated and described the principles of my invention in two alternative embodiments, in both males and females, it should be appreciated that additions and modifications may be made without departing from such principles. I claim all variations and modifications within the spirit and scope of the following claims.

I claim:

1. An implantable apparatus for controlling urinary incontinence in a patient, comprising:
   a reservoir containing fluid positionable subcutaneously over the patient's anterior pubis;
   inflatable compression means positionable intrapelvically above the patient's pelvic diaphragm between the patient's posterior pubic symphysis and urethra of occluding the urethra;
   conduit means arranged to extend over the patient's superior pubis through the abdominal wall between said reservoir and said compression means to provide fluid communication therebetween for inflating the compression means in response to fluid flow from said reservoir;
   said inflatable compression means being arranged to compress against the urethra and/or bladder neck along an extended area of only the anterior side thereof and including means for directing inflation of the balloon preferentially in a direction normal to the dimension of said cross-sectional shape so as to compress the urethra in an inferior-posterior direction.

2. Apparatus according to claim 1 further including means for anchoring said conduit means to the superior pubis.

3. Apparatus according to claim 1 further including a single check valve positioned in the conduit means between said reservoir and said compression means so that fluid discharged from the reservoir is retained in the compression means under pressure.

4. Apparatus according to claim 3 wherein said apparatus further includes means subcutaneously-positionable adjacent the reservoir on the anterior pubis accessible for manual external actuation by the patient to effect a reverse flow of fluid through said check valve to deflate the compression means and thereby permit voiding.

5. Apparatus according to claim 1 in which the compression means comprises an inflatable balloon having an oval cross-sectional shape.

6. An apparatus according to claim 1 in which the reservoir has an anterior sidewall including a self-sealing diaphragm for inserting a needle transcutaneously to modify the volume of fluid in the apparatus.

7. Apparatus according to claim 1 including means for affixing the patient's bladder to the patient's internal abdominal wall to secure the bladder in an elevated position such that the urethra is extended.

8. An implantable apparatus for controlling urinary incontinence in a patient, comprising:
a reservoir containing fluid positionable subcutaneously over the patient's anterior pubis;
inflatable compression means positionable intrapelvically above the patient's pelvic diaphragm between the patient's posterior pubic symphysis and urethra for occluding the urethra;
conduit means arranged to extend over the patient's superior pubis through the abdominal wall between said reservoir and said compression means to provide fluid communication therebetween for inflating the compression means in response to fluid flow from said reservoir;
said inflatable compression means being arranged to compress against the urethra and/or bladder neck along an extended area of only the anterior side thereof, the compression means comprising an inflatable balloon having a semirigid skirt surrounding an entrance portion of the balloon for directing the expansion of the balloon preferentially in a direction axially of the balloon from said entrance so as to compress the urethra in an inferior-posterior direction.

9. An implantable apparatus for controlling urinary incontinence in a patient, comprising:
a reservoir containing fluid positionable subcutaneously over the patient's anterior pubis;
inflatable compression means positionable intrapelvically above the patient's pelvic diaphragm between the patient's posterior public symphysis and urethra for occluding the urethra;
conduit means arranged to extend over the patient's superior pubis through the abdominal wall between said reservoir and said compression means to provide fluid communication therebetween for inflating the compression means in response to fluid flow from said reservoir;
said inflatable compression means being arranged to compress against the urethra and/or bladder neck along an extended area of only the anterior side thereof, the compression means comprising an inflatable balloon having a sidewall of variable thickness, the thickness being greatest in an entrance portion of the balloon and least in an end portion remote from the entrance of the balloon for directing the expansion of the balloon preferentially in a direction axially of the balloon from said entrance so as to compress the urethra in an inferior-posterior direction.

10. An implantable apparatus for controlling urinary incontinence in a patient, comprising:
a reservoir containing fluid positionable subcutaneously over the patient's anterior pubis;
inflatable compression means positionable intrapelvically above the pelvic diaphragm between the patient's posterior pubic symphysis and urethra and arranged to compress solely against the anterior side of urethra along an extended area for occluding the urethra;
conduit means providing fluid communication between said reservoir and said compression means for inflating the compression means in response to fluid flow from said reservoir and interconnecting the reservoir and compression means with said conduit means extending over the pubis;
valve means in the conduit means between said reservoir and said compression means for retaining fluid discharged from the reservoir in the compression means under pressure; and
means for directing inflation of said compression means preferentially in a posterior-inferior direction when said compression means is so positioned;
the valve means being positioned adjacent the reservoir for subcutaneous positioning therewith and including means externally actuable manually by the patient for releasing a reverse flow of fluid from the compression means to permit voiding.

11. Apparatus according to claim 10 in which the reservoir has a generally flattened, oblong shape including an anterior-posterior width and a lateral dimension sized greater than said width so as to overlie a broad expanse of the anterior pubis.

12. Apparatus according to claim 11 in which the reservoir and valve means are integrally formed with the valve means positioned adjoining an outlet of the reservoir so as to be located on the anterior pubis accessible for manual external actuation by the patient.

13. An apparatus according to claim 10 in which the reservoir has an anterior sidewall including a self-sealing diaphragm for inserting a needle transcutaneously to modify the volume of fluid in the apparatus.

14. Apparatus according to claim 10 in which the compression means comprises an inflatable balloon having a semirigid skirt surrounding an entrance portion of the balloon for directing the expansion of the balloon preferentially in a direction axially of the balloon from said entrance so as to compress the urethra in an inferior-posterior direction.

15. Apparatus according to claim 10 in which the compression means comprises an inflatable balloon having a sidewall of variable thickness, the thickness being greatest in an entrance portion of the balloon and least in an end portion remote from the entrance of the balloon for directing the expansion of the balloon preferentially in a direction axially of the balloon from said entrance so as to compress the urethra in an inferior-posterior direction.

* * * * *